(12) United States Patent
Eyckerman et al.

(10) Patent No.: US 8,343,932 B2
(45) Date of Patent: Jan. 1, 2013

(54) PROTEASE-SENSITIVE SITE IN APOLIPOPROTEIN A1, THERAPEUTIC AND DIAGNOSTIC IMPLICATIONS

(75) Inventors: Sven Eyckerman, De Pinte (BE); Koen Kas, Schilde (BE); Christine Labeur, Bruges (BE)

(73) Assignee: Pronota N.V., Zwijnaarde (BE)

( * ) Notice: Subject to any disclaimer, the term of this patent is extended or adjusted under 35 U.S.C. 154(b) by 243 days.

(21) Appl. No.: 12/738,282

(22) PCT Filed: Oct. 17, 2008

(86) PCT No.: PCT/EP2008/064054
§ 371 (c)(1),
(2), (4) Date: Apr. 15, 2010

(87) PCT Pub. No.: WO2009/050275
PCT Pub. Date: Apr. 23, 2009

(65) Prior Publication Data
US 2010/0222276 A1    Sep. 2, 2010

(30) Foreign Application Priority Data

Oct. 19, 2007  (EP) .................................... 07118859

(51) Int. Cl.
| | |
|---|---|
| *A61K 38/16* | (2006.01) |
| *C07K 14/00* | (2006.01) |
| *C07K 1/107* | (2006.01) |
| *C12Q 1/34* | (2006.01) |
| *A61P 9/10* | (2006.01) |

(52) U.S. Cl. ......... 514/21.2; 530/350; 530/402; 435/18; 435/7.1

(58) Field of Classification Search .................... 514/12, 514/21.2; 530/350, 402; 435/18, 7.1
See application file for complete search history.

(56) References Cited

U.S. PATENT DOCUMENTS

| 6,727,066 B2 * | 4/2004 | Kaser ........................ 435/6.14 |
|---|---|---|
| 2003/0108871 A1 | 6/2003 | Kaser |
| 2005/0287636 A1 | 12/2005 | Cho |

FOREIGN PATENT DOCUMENTS
WO    WO 03/035691    5/2003

OTHER PUBLICATIONS

Database Geneseq [Online], "Variant Human Apolipoprotein (apoA-I), A158E," Feb. 23, 2006, retrieved from EBI accession No. GSP:AEE87850, Database accession No. AEE87850.
Database Geneseq [Online], "Human Protein Expressed in a Liver Disorder #8," Jan. 29, 2004, retrieved from EBI accession No. GSP:ADE76862, Database accession No. ADE76862.
Gevaert, et al. "Protein Processing and Other Modifications Analyzed by Diagonal Peptide Chromatography," *Biochimica et Biophysica Acta*, vol. 1764, No. 12, pp. 1801-1810, Dec. 14, 2006.
Gevaert, et al. "Diagonal Reverse-phase Chromatography Applications in Peptide-centric Proteomics: Ahead of Catalogue-omics?," *Analytical Biochemistry*, vol. 345, No. 1, pp. 18-29, Oct. 1, 2005.
Sandra, et al. "Combination of COFRADIC and High Temperature-extended Column Length Conventional Liquid Chromatography: A Very Efficient Way to Tackle Complex Protein Samples, Such as Serum," *Journal of Separation Science*, vol. 30, No. 5, pp. 658-668, Mar. 2007.
Ye, et al. "Influence of Genetic Polymorphisms on Responsiveness to Dietary Fat and Cholesterol," *The American Journal of Clinical Nutrition*, vol. 72, No. 5 Suppl. pp. 1275S-1284S, Nov. 2000.
International Search Report dated Feb. 9, 2009 issued to international application No. PCT/EP2008/064054.

* cited by examiner

*Primary Examiner* — Chih-Min Kam
(74) *Attorney, Agent, or Firm* — Knobbe, Martens, Olson & Bear, LLP

(57) ABSTRACT

The invention relates to the identification of a naturally occurring internal proteolytic cleavage site in the ApoA1 protein, which leads to inactivation of the mature protein. Specific modification of this cleavage site leads to a stabilised ApoA1 protein, which is beneficial for the reverse cholesterol transport. The invention therefore encompasses pharmaceutical compositions comprising a recombinant stabilised variant ApoA1 protein or rHDL particles comprising such a protein, for use in the treatment of patients having reduced HDL or hampered reverse cholesterol transport.

9 Claims, 3 Drawing Sheets

Fig 2a

```
1    agagactgcg agaaggaggt cccccacggc ccttcaggat gaaagctgcg gtgctgacct
61   tggccgtgct cttcctgacg gggagccagg ctcggcattt ctggcagcaa gatgaacccc
121  cccagagccc ctgggatcga gtgaaggacc tggccactgt gtacgtggat gtgctcaaag
181  acagcggcag agactatgtg tcccagtttg aaggctccgc cttgggaaaa cagctaaacc
241  taaagctcct tgacaactgg gacagcgtga cctccacctt cagcaagctg cgcgaacagc
301  tcggccctgt gacccaggag ttctgggata acctggaaaa ggagacagag ggcctgaggc
361  aggagatgag caaggatctg gaggaggtga aggccaaggt gcagccctac ctggacgact
421  tccagaagaa gtggcaggag gagatggagc tctaccgcca gaaggtggag ccgctgcgcg
481  cagagctcca gagggcgcg cgccagaagc tgcacgagct gcaagagaag ctgagcccac
541  tgggcgagga gatgcgcgac cgcgcgcgcg cccatgtgga cgcgctgcgc acgcatctgg
601  cccctacag cgacgagctg cgccagcgct tggccgcgcg ccttgaggct ctcaaggaga
661  acggcggcgc cagactggcc gagtaccacg ccaaggccac cgagcatctg agcacgctca
721  gcgagaaggc caagcccgcg ctcgaggacc tccgccaagg cctgctgccc gtgctggaga
781  gcttcaaggt cagcttcctg agcgctctcg aggagtacac taagaagctc aacacccagt
841  gaggcgcccg ccgccgcccc ccttcccggt gctcagaata aacgtttcca aagtggg
```

Nucleotide sequence of the coding region of the human ApoA1 gene

Fig 2b

```
1    mkaavltlav lfltgsqarh fwqqdeppqs pwdrvkdlat vyvdvlkdsg rdyvsqfegs
     |pre                |pro    |mature protein
61   algkqlnlkl ldnwdsvtst fsklreqlgp vtqefwdnle keteglrqem skdleevkak
121  vqpylddfqk kwqeemelyr qkveplrael qegarqklhe lqekslplge emrdrarahv
181  dalrthlapy sdelrqrlaa rlealkengg arlaeyhaka tehlstlsek akpaledlrq
241  gllpvlesfk vsflsaleey tkklntq
```

Amino acid sequence of the coding region of the human ApoA1 gene

PROTEASE-SENSITIVE SITE IN APOLIPOPROTEIN A1, THERAPEUTIC AND DIAGNOSTIC IMPLICATIONS

CROSS-REFERENCE TO RELATED APPLICATIONS

This application is the U.S. National Phase under 35 U.S.C. §371 of International Application PCT/EP2008/064054, filed Oct. 17, 2008, which claims priority to EP 07118859.3, filed Oct. 19, 2007.

FIELD OF THE INVENTION

The invention is generally related to lipid metabolism, particularly to HDL-related lipid metabolism involving apolipoprotein A1 (ApoA1). The invention further relates to the provision of a medicament to improve the cholesterol balance of a patient and to methods for diagnosing or analysing the cholesterol balance of a patient.

BACKGROUND OF THE INVENTION

Apolipoprotein A1 (ApoA1) is together with ApoE an essential component of High Density Lipoprotein particles (HDL), and contributes to formation of the so called 'good' cholesterol, as opposed to the Low Density Lipoprotein particles (LDL), often referred to as 'bad' cholesterol, composed of ApoB-100, ApoC, ApoE and Apo(A). ApoA1 is a single polypeptide chain consisting of 243 amino acids, synthesised in the liver and the intestine in the form of a pre-pro-protein of 267 amino acid residues (cf. SEQ ID NO:1 (nucleotide sequence) and SEQ ID NO:2 (amino acid sequence) and FIGS. 2a and 2b respectively). The pre-pro-protein is cleaved into a pro-protein that is secreted into the plasma. In the vesicular blood structure, the pro-protein is subsequently processed into its mature (243 AA) form by a calcium-dependent protease (FIG. 2b).

The balance between HDL-cholesterol and LDL-cholesterol in the blood is of the outmost importance to prevent atherosclerosis and related cardiovascular diseases. It has been known for some time that a low level of HDL-cholesterol leads to an increased risk of atherosclerosis, due to the anti-atherosclerosis and anti-hyperlipidemia effect of HDL by stimulating a reverse cholesterol transport (RCT) pathway from the peripheral tissue to the liver.

The sequence of events in RCT is likely as follows (Ohashi et al., QJM. 98(12):845-56, 2005) ApoA-I is produced mainly by the liver, and released into the plasma. Circulating ApoA-I interacts with serum phospholipids and forms nascent discoidal HDL (ndHDL). Once ndHDL is generated, it triggers cholesterol efflux in the macrophages and fibroblasts in the subendothelial space. Externalized cholesterol is absorbed by ndHDL, and subsequently esterified by lecithin:cholesterol acyltransferase (LCAT). HDL particles are enriched with cholesteryl ester and become larger, resulting in HDL3 and HDL2. Phospholipid transfer protein (PLTP) is involved in this process: for example, by fusing two HDL3 into one HDL2 molecule. If HDL molecules are enriched with triglyceride, they are processed by the enzyme hepatic lipase (HL) and become smaller and denser. HL can convert the phospholipid-rich HDL2 to HDL3. However, regulation of the balance of HL and PLTP is not clear. Cholesterol ester transfer protein (CETP) facilitates the equimolar exchange of cholesteryl esters from HDL for triglycerides in apoB100-containing lipoproteins. These cholesteryl esters are then delivered back to the liver via low-density-lipoprotein receptor (LDL-R), converted to bile salts, and eliminated through the gastrointestinal tract.

In addition to this process, when acceptors such as apoA-I and HDL approach macrophages in subintimal space, intracellular cholesterol is released outside the cells for excretion, a process termed cholesterol efflux of macrophages. In this pathway, ATP-binding membrane cassette transport protein A1 (ABCA1) plays a major role in translocating cholesterol into the extracellular space. In addition to ABCA1, four other factors are known to be involved in the pathway. Scavenger receptor B1 (SR-B1) can induce cholesterol efflux by enabling HDL to bind to cells and reorganize lipids within cholesterol-rich domains in the plasma membrane. Caveolins are typically associated with caveolae, which are non-clathrin-coated plasma membrane microdomains rich in cholesterol and glycosphingolipids. Caveolins are small proteins (18-24 kDa) that have a hairpin loop conformation, with both the N and C termini exposed to the cytoplasm. These proteins have the capacity to bind cholesterol, and can transport cholesterol from the endoplasmic reticulum to the plasma membrane. A report showed that over-expression of caveolins enhances cholesterol efflux in hepatic cells without affecting ABCA1 expression, indicating the presence of a caveolin-dependent pathway. Sterol 27-hydroxylase (CYP27A1) is also known as a contributor to cholesterol efflux. CHO cells transfected with CYP27A1 showed increased cholesterol efflux. Since ABCA-1 expression was not altered, CYP27A1 could cause cholesterol efflux independent of other factors. In addition to these pathways, cholesterol efflux can also occur via passive diffusion, in which cholesterol is desorbed down to the concentration gradient onto acceptor molecules. Thus, RCT and cholesterol efflux constitute an efficient pathway by which excess cholesterol can be removed out of the body. Although extensive studies have recently been performed, RCT is a complicated process and its regulation mechanisms are largely unknown. Several key factors described above are involved in the RCT and cholesterol efflux, but the interrelationship among these factors is not clear.

The role of ApoA1 in this process has been well established over the years and several studies have been directed to the possibilities of administration of recombinant ApoA1 peptide fragments or even full length proteins to subjects with low HDL-cholesterol levels, other dyslipidemic disorders or cardiovascular disease. In order to increase stability of the ApoA1 protein, even thermostabilisation in the presence of chaotropic agents has been tried.

In addition, peptidomimetics of ApoA1 have also been designed that beneficially influence the lipid parameters and/or cholesterol levels in the blood. Several ApoA1 agonists have also been developed in order to mimic the function of ApoA1.

A recombinant ApoA1 mutant protein (the 'milano' mutant) is currently under investigation in the treatment of cardiovascular disease (Nissen et al. JAMA 290: 2292-2300, 2003). This mutant ApoA1 has an Arginine to Cysteine mutation at amino acid position 197 (R197C) in the pre-pro-ApoA1 protein amino acid sequence (corresponding to R173C in the mature ApoA1 amino acid sequence). The cysteine in the milano mutant leads to the formation of an ApoA1 dimer, held together by a disulfide bond, due to the additional cysteine residue. It has been established that administration of "nascent" HDL particles reconstructed in vitro by combining phopsholipids and the milano ApoA1 protein to patients leads to a significant decrease in plaque formation. These particles take up the esterified cholesterol from the lipid loaded plaques thereby reducing the size of the atherosclerotic plaques. A similar variant, the ApoA1 'paris' variant has also been identified and has a similar mutation of Arginine to Cysteine, on position 175 (R175C) of the pre-pro-protein (corresponding to R151C in the mature ApoA1 amino acid sequence). The process of making such ApoA1 milano dimers recombinantly or purifying it from plasma samples from carrying humans is however quite cumbersome, in part because of degradation of the protein.

There is therefore clearly a need for a stabilised Apo A1 protein variant that is easy to make recombinantly for use in medicine in the form of a pharmaceutical preparation that improves the inverted cholesterol transport in a patient.

SUMMARY OF THE INVENTION

The goal of this invention is to provide a stabilised variant of the ApoA1 protein that improves the inverted cholesterol transport in a subject and subsequently ameliorates the cholesterol balance in subjects suffering from e.g. a high level of cholesterol in their blood circulation due to low HDL levels. The invention provides a stabilised ApoA1 protein for use in medicine, possibly in the form of a pharmaceutical preparation.

The invention thus provides a method for producing a stabilised, protease resistant ApoA1 protein variant comprising:
a) modifying the ApoA1 protein either by amino acid substitution or by chemical modification of the amino acid side chains at a position surrounding the R184 position in the amino acid sequence of ApoA1 (SEQ ID NO: 2, FIG. 2b); and
b) analysing the proteolytic cleavage of the ApoA1 variant; and optionally
c) analysing the LCAT activation efficiency of the Apo1A variant.

The invention also provides a recombinant stabilised ApoA1 protein variant modified in a position surrounding the R184 position in the amino acid sequence of ApoA1 (SEQ ID NO: 2, FIG. 2b), which is protease-resistant and wherein one or more modifications are done at a position selected from the group of: D181, A182, L183 R184, T185 and H186. In a preferred embodiment, of the recombinant stabilised ApoA1 protein variant according to the invention, the one or more modifications are mutations selected from the group of: A182G, A182V, L183I, L183V, R184P, R184K, R184H, T185N, T185Q, T185S, T185Y, H186R, H186L, based on (SEQ ID NO: 2, FIG. 2b).

The invention further provides for a reconstituted HDL (rHDL) particle comprising at least one recombinant protease-resistant ApoA1 variant according to the invention and its use as a medicament or in the manufacturing of a medicament.

Additionally, the invention provides a recombinant protease-resistant ApoA1 protein variant or reconstituted HDL particle according to the invention for use as a medicament.

Said medicament can preferably be a medicament that improves the cholesterol balance of a patient. Alternatively, said medicament can preferably be a medicament that is used for treating dyslipidemia, hyperlipidemia, hypercholesterolemia, hypertriglyceridemia, hyperlipoproteinemia, HDL deficiency, ApoA-I deficiency, cardiovascular disease, coronary artery disease, angina, myocardial infarction, sudden cardiac death, atherosclerosis, restenosis, atherosclerotic plaques, atherosclerotic plaques resulting from medical procedures such as balloon angioplasty Alternatively, said medicament can be a medicament that is used for treating a disease selected from the group comprising: infections due to bacteria, endotoxemia, septic shock, infections due to viruses, influenza A, influenza B, inflammation, Alzheimer's disease and age-related macular degeneration (AMD).

The invention further provides a method for identifying the protease responsible for the cleavage of wild type human ApoA1 at the R184 position of the prepro-ApoA1 amino acid sequence as defined in SEQ ID NO: 2 (FIG. 2b) comprising:
a) providing the isolated wild-type ApoA1 protein
b) providing a candidate protease
c) analysing the proteolytic cleavage of the wild-type ApoA1 protein at its R184 position in the presence and absence of the protease thereby analysing the ability of the protease under investigation to cleave ApoA1 at its R184 position.

The invention further provides a method for screening agents that inhibit the cleavage of the wild type human ApoA1 at the R184 position of the pre-pro-ApoA1 amino acid sequence as defined in SEQ ID NO: 2 (FIG. 2b), comprising:
a) providing the isolated wild-type ApoA1 protein
b) providing an agent
c) analysing the proteolytic cleavage of the wild-type ApoA1 protein at its R184 position in the presence and absence of the agent, thereby analysing the inhibitory effect of the screened agent.

The invention further provides a method for stabilising a known pharmaceutical composition in which the ApoA1-protein or variant or modified protein is the active ingredient, the method comprising modifying the ApoA1 protein in a position surrounding the R184 position in the amino acid sequence of ApoA1 (SEQ ID NO: 2, FIG. 2b) either by amino acid substitution or by chemical modification of the amino acid side chains in such a way that proteolytic cleavage of the active ingredient is blocked. In a preferred embodiment, said active ingredient is a recombinant ApoA1 protein variant, a rHDL particle comprising a recombinant ApoA1 protein variant or a multimer of ApoA1 protein variants.

In addition, the invention provides a method for analysing the cholesterol balance in a subject comprising the detection of a mutation in isolated ApoA1 of a subject leading to a stabilisation or increased half-life of the protein, wherein the mutation is an amino acid deletion, introduction or substitution situated around amino acid position 184 of the prepro-ApoA1 amino acid sequence as defined in SEQ ID NO: 2, wherein detection of such a mutation points to a changed cholesterol balance in the patient. In a preferred embodiment, the mutation is an Arg to Pro modification at amino acid position 184 of the prepro-ApoA1 amino acid sequence as defined in SEQ ID NO: 2 (FIG. 2b), wherein detection of the mutation points to a favourable cholesterol balance in the patient due to stabilisation of the ApoA1 protein. One possible example of such a mutation can be the R184 to P mutation reported below.

The invention further provides a composition comprising a recombinant protease-resistant ApoA1 protein variant or modified protein or reconstituted HDL (rHDL) particles encompassing such a recombinant ApoA1 variant or modified protein and the use of said compositions as a medicament or in the manufacturing of a medicament to improve the cholesterol balance of a subject.

In addition, the invention provides a method for identifying the protease responsible for the cleavage of the ApoA1 protein and for screening methods identifying small molecules or other agent that target said protease involved with the degradation of ApoA1. Such agents would be useful for the stabilisation of the endogenous protein, not requiring the production and administration of a recombinant form when the endogenous protein is present.

The invention further relates to the stabilisation of other known ApoA1 recombinant proteins that are used or that will be used for therapeutic applications can be produced, with the potential to significantly reduce dosing of these proteins, comprising the modification of the proteolytic cleavage site at or around the 184 position of ApoA1.

The invention further provides a method for treating a diseases or disorder linked to ApoA1 comprising administering to a patient a pharmaceutically active amount of the recombinant protease-resistant ApoA1 variant or reconstituted HDL particle according to the invention. In a preferred embodiment, said disease is related to cholesterol balance. In a further preferred embodiment said disease is selected from the group comprising: dyslipidemia, hyperlipidemia, hypercholesterolemia, hypertriglyceridemia, hyperlipoproteinemia, HDL deficiency, ApoA-I deficiency, cardiovascular disease, coronary artery disease, angina, myocardial infarction, sudden cardiac death, atherosclerosis, restenosis, atherosclerotic plaques, atherosclerotic plaques resulting from medical procedures such as balloon angioplasty.

In an alternative embodiment, said disease is selected fromp the group consisting of infections due to bacteria, endotoxemia, septic shock, infections due to viruses, influenza A, influenza B, inflammation, Alzheimer's disease and age-related macular degeneration (AMD).

The number of peptides identified by N-terminal COFRADIC and their corresponding starting position in the pre-pro-ApoA1 protein. The sample used is serum obtained from a healthy volunteer. The number of peptide identifications gives a rough estimate on the extent of cleavage at the particular position, showing thus extensive cleavage in the pre-pro-ApoA1 protein after R184. The protein and its processed form are shown schematically below the graph.

FIG. 2:

FIG. 2a shows the complete nucleotide sequence of the mRNA encoding the pre-pro-ApoA1 protein, available as NM_000039 in Genbank.

FIG. 2b shows the amino acid sequence of the pre-pro ApoA1 protein, available as NP_000030 in Genbank and indicates the starting points of the pre-form (starting at AA residue 1, pro-form (starting at AA residue 19) and the mature ApoA1 protein (starting at AA residue 25).

FIG. 3:

Western blot for ApoA-1 isoforms present in depleted serum of human male donors. The AI-4.1 mouse monoclonal antibody directed at the C-terminus of ApoA-1 reveals the mature ApoA-1 and a fragment of about 10 kDa.

DETAILED DESCRIPTION OF THE INVENTION

The inventors used N-terminal peptide-identification technologies to identify novel N-termini that are generated by proteolysis. Protein cleavage is an important step in degradation, and appears to be an essential process in serum or plasma homeostasis.

It has to be emphasized that throughout the description and the claims, the amino acid sequence of the pre-pro-ApoA1 protein (SEQ ID NO: 2, FIG. 2b) is used and not the amino acid sequence of the mature ApoA1 protein, which is 24 amino acid residues shorter in its N-terminal region. This is important for the exact positioning of the amino acid residues mentioned further.

Figure 1:
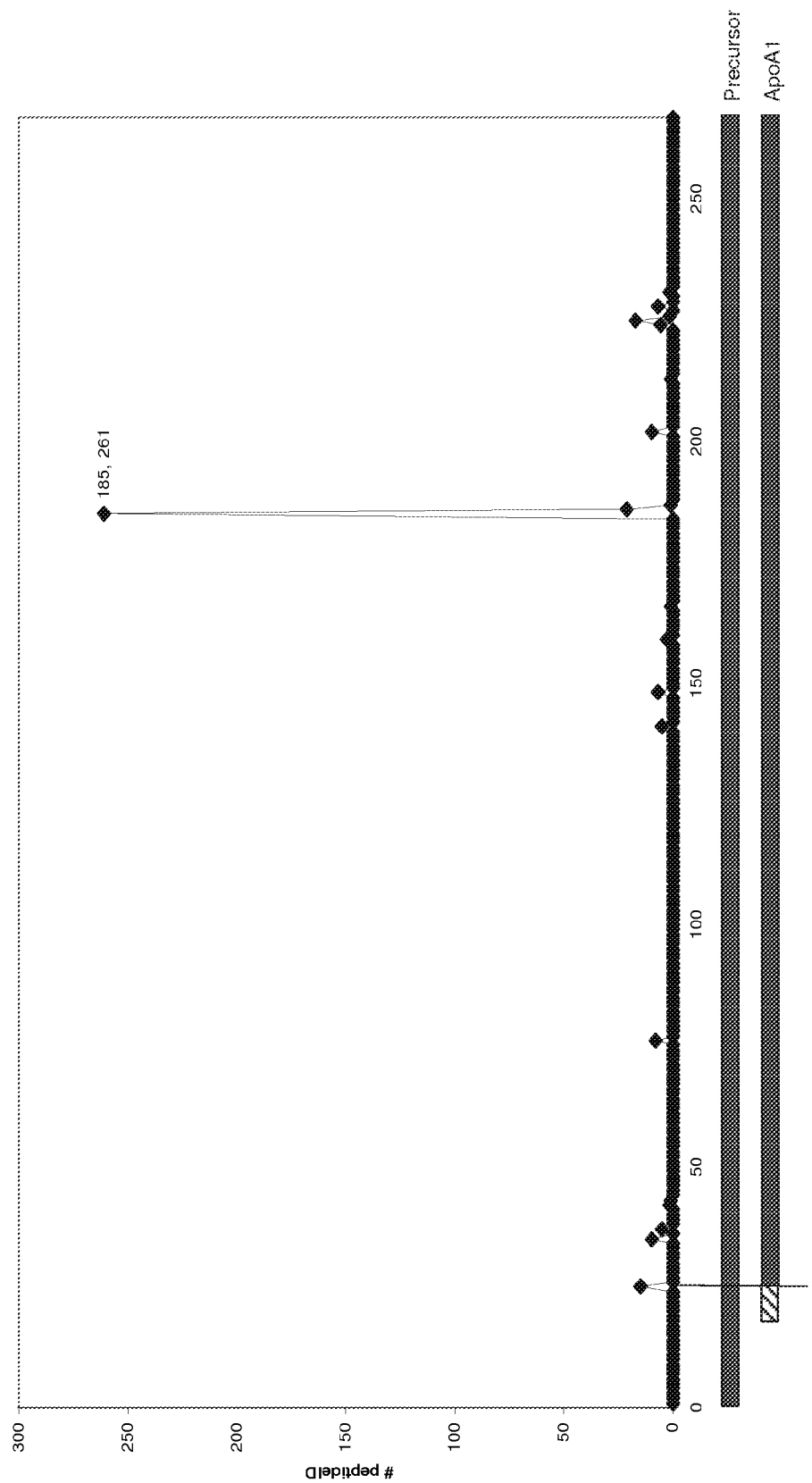
FIG. 1.
Figure 3:
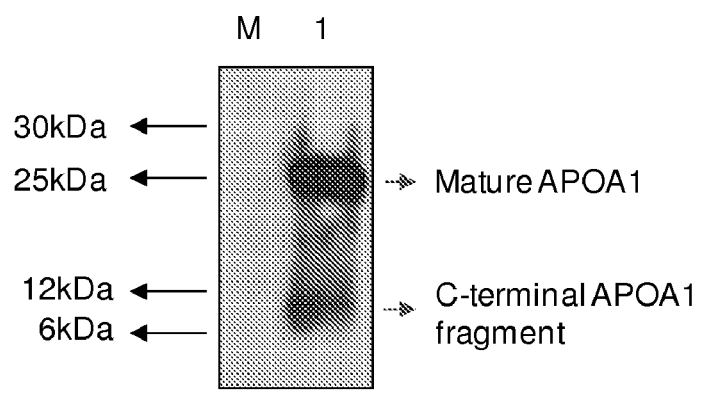

By detailed analysis of the proteolytic pattern generated for ApoA1, the inventors detected that next to the pre-pro cleavage of the ApoA1 protein at position 24, an additional ApoA1 fragment that starts at amino acid position 185 is present in serum samples of healthy human subjects (FIG. 1). This implies that the wild type protein undergoes extensive proteolysis after position R184 (Arginine at position 184) of the pre-pro-ApoA1 amino acid sequence (SEQ ID NO: 2, FIG. 2b). This proteolysis likely results in the physical dissociation of two different functional domains of the protein, thereby inactivating it. One of these domains is important for cholesterol loading and the other is needed for cholesterol transport. When ApoA1 is cleaved by its yet unknown naturally occurring protease, the cholesterol efflux activity of ApoA1 appears to be lost.

The invention therefore provides a method to stabilise the ApoA1 protein, by blocking the naturally occurring cleavage of ApoA1 at its R184 position. This results in an ApoA1 variant or modified protein, with an increased half-life in vivo and can be used in a composition which is beneficial for patients suffering from deficient reverse cholesterol transport, cholesterol efflux, or patients suffering from cardiovascular conditions, atherosclerosis due caused by e.g. high fat diets or in obese subjects. The compositions of the invention could also be used as a food additive for such patients or even for healthy subjects, to prevent future cholesterol-related problems and disorders.

The invention further provides a method for identifying the protease responsible for the cleavage of wild type human ApoA1 at the R184 position of the pre-pro-ApoA1 amino acid sequence as defined in SEQ ID NO: 2, (FIG. 2b) comprising:
a) providing the isolated wild-type ApoA1 protein,
b) providing a candidate protease,
c) analysing the proteolytic cleavage of the wild-type ApoA1 protein at its R184 position in the presence and absence of the protease using the method of the invention, thereby analysing the ability of the protease under investigation to cleave ApoA1 at its R184 position.

In addition, the invention provides a method for screening agents that inhibit the cleavage of the wild type human ApoA1 at the R184 position of the prepro-ApoA1 amino acid sequence as defined in SEQ ID NO: 2 (FIG. 2b), comprising:
a) providing the isolated wild-type ApoA1 protein
b) providing an agent
c) analysing the proteolytic cleavage of the wild-type ApoA1 protein at its R184 position in the presence and absence of the agent using the method of the invention, thereby analysing the inhibitory effect of the screened agent.

Recently a further ApoA1 mutant was reported in a Norwegian family, called the ApoA1 'Oslo' mutant. This naturally occurring ApoA1 variant has an R184L mutation and carriers of the mutant ApoA1 'Oslo' have low HDL levels in their blood and an increased risk of developing atherosclerosis. Functional analysis of this mutant showed that it was largely unable to activate LCAT, but that it retained at least some of its cholesterol efflux capacities (Leren et al., J Lipid Res. 1997 January; 38(1):121-31). In another report, it was hypothesized that the R184 residue, together with the R173 and R177 residues are structurally important residues for the activation of LCAT, because of their position in the three-dimensional structure of the ApoA1 protein. In the proposed 'belt'-model, residues R173, R177, and R184 are pointing toward the surface of the disc, enabling interactions with LCAT (Roosbeek et al., J Lipid Res. 2001 January; 42(1):31-40). Some further mutants in the proximity of R184 have been reported as well e.g. the L183P 'Zavalla' mutant and the R184V/H186A double mutant. Both mutants are known to have hampered LCAT activation capacities.

Due to the importance of the region surrounding the R184 and the data obtained in our proteolysis assay, the inventive concept is directed to the modification of the ApoA1 protein at its R184 position or at neighbouring positions in such a way that the naturally occurring proteolytic cleavage is hampered or blocked. This blocking can be either done by chemical modification of the amino acid side chains or by introduction of specific point mutations leading to amino acid substitutions. In principle, any one or more of the amino acid residues at positions 182-185 of the ApoA1 protein can be modified or substituted by any of the other 19 available amino acid residues.

The term "surrounding" should be interpreted as being either one of 0, 1, 2, or 3 amino acid positions before or after the indicated amino acid position.

Such a modification could however result in a reduction or even loss of LCAT activation capacity, which is undesirable.

To compensate this, the modified proteins of the invention can be administered in combination with LCAT, either purified or recombinantly made, in order to compensate for the loss of LCAT activation capacity of the modified ApoA1 protein variant or modified protein, which has previously been shown to have beneficial effects on patients suffering from cholesterol-related disorders (Koukos et al., Biochem J. 406(1):167-74) to compensate the lack of LCAT activation of recombinant modified ApoA1 proteins.

Alternatively, the modification process itself can be tailored in such a way that the LCAT activation function of the ApoA1 variant or modified protein is completely or at least partially preserved.

In this respect, it can be noted from several reports that many functionally inactive mutants of ApoA1 carry an amino acid substitution with a member of a different family of amino acid residues which results in an important structural change. Examples are the R184L 'Oslo' and the R184V mutations, substituting a basic amino acid residue with a non-polar amino acid residue, the A182E mutation, substituting a non-polar amino acid residue with an acidic amino acid residue and the H186A mutation, substituting a basic amino acid residue with a non-polar amino acid residue. These substitutions all lead to a loss of LCAT-activation capacity of the ApoA1 mutants.

Avoiding loss of LCAT-activation function of the ApoA1 protein can therefore be accomplished by introducing specific point mutations or amino acid deletions or insertions changing the amino acid sequence of the ApoA1 protein, without changing its structure in a drastic manner e.g. by substituting the amino acids with structurally related amino acids (e.g. basic, acidic, uncharged or non-polar amino acids are substituted by other respectively basic, acidic, uncharged or non-polar amino acids). In a preferred embodiment, the mutation is selected from the group of A182G, A182V, L183I, L183V, R184P, R184K, R184H, T185N, T185Q, T185S, T185Y, H186R, H186L mutations. In a most preferred embodiment, the mutation is R184P, R184K or R184H.

In a second approach, the amino acid side chains of the R184 or its neighbouring amino acid residues can be modified in such a way that the protease is hampered in the cleavage process of ApoA1, e.g. due to sterical hindrance. These side chain modifications are less drastic than actually changing the primary structure of the ApoA1 protein and will more likely result in functional (i.e. LCAT activation capacity) preservation. Oxidation, reduction, acetylation, etc. can be used. Further examples are the modification of Arginine side chains by using HPG (p-Hydroxyphenylglyoxal), which is an Arginine selective modifying agent or of Tryptophan residues using Tryptophan side chain oxidase II.

In this respect, it is noteworthy that the R184 residue is pointed towards the outside of the protein in the so called 'belt' model (Roosbeek et al., J Lipid Res. 2001 January; 42(1):31-40). This implies that modification of the Arginine side chains by a chemical process would be largely limited to these Arginine residues, not influencing the remaining Arginines in the molecule.

The ApoA1 variants or modified proteins of the invention can be subsequently tested for their stability in blood in vitro and in vivo, and their effect on reverse cholesterol transport in both in vitro and in vivo methods as described further in the application.

LCAT activation assays known in the art can also be used to test the ability of the ApoA1 variants or modified proteins of the invention to activate LCAT, an important function of ApoA1 proteins in vivo. Methods for determining LCAT activation have been described, for example, in U.S. Pat. Nos. 6,004,925, 6,046,166 and 6,037,323.

If the modified ApoA1 protein resulting from the above disclosed methods would be unable to activate LCAT, this negative effect could e.g. be compensated by combining LCAT itself in a composition with the modified ApoA1 protein, for use as a pharmaceutical composition, or by using an LCAT activating molecule or chemical agent.

In addition, several tests for the effect of the ApoA1 protein variants or modified proteins of the invention on cholesterol efflux and atherosclerosis can be used. One of these techniques is the in vitro analysis of a blood sample, out of which the monocyte population is isolated, followed by measuring the amount of cholesterol efflux in the macrophages cells of a subject. Another possibility is to analyse the level of plasma HDL-cholesterol before and after the administration of the compositions of the invention. An increase of HDL-cholesterol in the serum after administration of the composition of the invention points towards an increased cholesterol efflux.

In addition, an in vitro test of cholesterol efflux from cholesterol loaded hepatoma cells can be used to analyse the effect of the compositions of the invention of cholesterol efflux. Such an assay is performed using hepatoma cells such as rat Fu5AH hepatoma cells following the procedure previously described by de la Llera Moya and co-workers (J. Biol Chem. 270(22):13004-13009, 1995). Briefly, the cells are maintained in minimal essential medium (MEM) containing 5% calf serum. 20,000 Fu5AH cells/ml are plated on 2.4 cm multiwell plates (Linbro, Polylabo) using 2 ml/well. Two days after plating, cellular cholesterol (approximately 25 µg/well) is labeled during a 48-h incubation with [3H]cholesterol (NEN, Dupont de Nemours) (1 µCi/well). To allow equilibration of the label, the cells are rinsed and incubated for 24 h in MEM containing 0.5% bovine serum albumin. For determination of cholesterol efflux, the cells are washed with phosphate-buffered saline and incubated at 37° C. with isolated HDL fractions diluted in MEM without albumin supplementation. At the end of the efflux period, medium is removed and centrifuged. Cell monolayer is washed three times with phosphate-buffered saline and harvested with 0.5 ml of 0.1 mol/liter NaOH. Finally, radioactivity is measured in both medium and cells, allowing the determination of the total radioactivity content in each well. Fractional cholesterol efflux, expressed as percent, is then calculated as the amount of label recovered in the medium divided by the total label in each well.

Since hampered or insufficient cholesterol efflux leads to atheroma formation, and increase reverse cholesterol transport actually reduces the volume of atheroma's in patients, the measurement of atheroma volume in vivo is also an important indication of activity of the compositions of the invention. Several tools are available to measure atheroma volume e.g. before and after the treatment with the compounds of the invention (reviewed by Nissen in European Heart Journal Supplements Vol. 6, Suppl C:C15-C20). Traditional techniques such as angiography could be used, but only provide information about lumen size and are thus of limited use in predicting clinical events. Improved understanding of the mechanisms underlying atherogenesis has resulted in the development of several potential techniques for assessing the disease process in humans. These include modalities that detect early structural changes in the coronary arteries, such as electron-beam-computed tomography, magnetic resonance imaging, and intra-vascular ultrasound; and those that detect surrogate markers for coronary atherosclerosis, such as the external vascular ultrasound measurement of carotid intima-media thickness.

Intra-vascular ultrasound or IVUS uses high-frequency ultrasound to image not only the coronary lumen but also the structure of the vessel wall, including the atherosclerotic plaque. IVUS has several inherent advantages for the precise quantification of atherosclerotic coronary disease. Firstly, because of its tomographical orientation, IVUS allows the full 360° circumference of the vessel wall to be visualized. This means that lumen dimensions can be directly planimetered on a cross-sectional image. Secondly, the tomographical perspective of ultrasound allows the precise assessment of vessels that are often difficult to assess angiographically. Thirdly, the frequency range of modern ultrasound systems (20-45 MHz) allows excellent resolution of structures within the artery wall. IVUS has great potential as a means of accurately assessing the atherosclerotic disease process, since it has the ability to demonstrate changes in atheroma volume over a relatively short period of time, with fewer patients than required for large morbidity and mortality end-point trials. It is safe, and gives accurate and reproducible measurements.

An alternative method is the carotid intima-media thickness (CIMT) measurement method, which is a simple technique. It uses a transcutaneous transducer, operating in the 7-10 MHz range, to visualize the carotid artery, where the target of measurement is the thickness of the intima-media complex. Using this technique, the carotid artery is viewed as a 'window' on the coronary arteries, since the risk factors that affect CAD also affect disease in the carotid arteries, and it has long been known that the presence of carotid disease is a powerful predictor of future coronary events. CIMT is a well-validated method for evaluation of the presence and extent of vascular disease. The technique is non-invasive, has no known biological hazards, is inexpensive, and the equipment is available in most clinical environments. CIMT also has a strong association with clinical outcome, and its ability to predict risk has been validated in large, carefully studied populations.

In addition, electron-beam-computed tomography (EBCT) is currently the technique of choice for evaluating atheroma calcification, and has become widely used for non-invasive direct coronary imaging. Studies have shown that the presence of calcification almost invariably indicates the presence of CAD and that the absence of calcification can nearly rule out significant CAD. Moreover, a correlation exists between the amount of calcification and the severity of CAD. Early studies of EBCT used angiography for comparison, which may not have been ideal, since most CAD is extra-luminal. Despite this, studies have shown that there is a correlation between the prevalence of angiographically significant disease and the amount of calcium in the coronary arteries. In some studies, EBCT-derived calcium score has been shown to be a better predictor of cardiovascular events than angiography.

In vivo, high-resolution, multi-contrast magnetic resonance imaging (MRI) is another promising method of non-invasively imaging vulnerable plaques, and determining different plaque components—such as lipid core, fibrosis, calcifications and thrombosis deposits—in large arteries. MRI findings have been extensively validated against pathology in ex vivo studies of carotid, aortic and coronary artery autopsy specimens. Imaging of carotid arteries in vivo in patients referred for endarterectomy showed a high correlation with pathology and with previous ex vivo results. Atherosclerotic assessment by MRI can lend itself for use as a screening tool for prediction of future cardiovascular events, and for further evaluation of therapeutic intervention benefits.

Pharmaceutical Compositions of the Invention

The invention encompasses pharmaceutical compositions or preparations comprising an ApoA1 variant or modified proteins according to the invention and a pharmaceutically acceptable carrier as a drug for improving the reverse cholesterol transport in a subject suffering from low HDL disorders. In a preferred embodiment, the protein is modified at a position surrounding the R184 position in the amino acid sequence of ApoA1 (SEQ ID NO: 2, FIG. 2b). In a more preferred embodiment, the therapeutic composition comprises the mutated ApoA1 protein selected from the group of A182G, A182V, L183I, L183V, R184P, R184K, R184H, T185N, T185Q, T185S, T185Y, H186R, H186L mutations, based on SEQ ID NO: 2 (FIG. 2b). In a most preferred embodiment, the mutation is R184P, R184K or R184H, based on SEQ ID NO: 2 (FIG. 2b). Administration of such a composition of the invention can result in a beneficial cholesterol balance for people in need thereof.

The pharmaceutical compositions can have as the active ingredient a recombinant ApoA1 variant or modified proteins according to the invention or alternatively, the composition comprises as the active ingredient an ApoA1 variant or modified proteins according to the invention in combination with a lipid compound. In one embodiment, this protein/lipid complex is in the form of a reconstituted HDL particle (rHDL) comprising an ApoA1 variant or modified proteins according to the invention as the active ingredient of the pharmaceutical composition. The ApoA1 variants or modified proteins of the invention can be included in the compositions in either the form of free acids or bases, or in the form of pharmaceutically acceptable salts. With pharmaceutical composition is meant any pharmaceutical composition known to those of skill in the art.

Injectable compositions include sterile suspensions, solutions or emulsions of the active ingredient in aqueous or oily vehicles. The compositions can also contain formulating agents, such as suspending, stabilizing and/or dispersing agent. The composition for injection can be presented in unit dosage form, e.g., in ampules or in multidose containers, and can contain added preservatives, in powder form for reconstitution with a suitable vehicle, including but not limited to sterile pyrogen free water, buffer, dextrose solution, etc., before use. To this end, the ApoA1 variants or modified proteins of the invention protein can be lyophilized, or the co-lyophilized protein-lipid complex can be prepared. The stored compositions can be supplied in unit dosage forms and reconstituted prior to use in vivo. For prolonged delivery, the ApoA1 variants or modified proteins of the invention can be formulated as a depot composition, for administration by implantation; e.g., subcutaneous, intradermal, or intramuscular injection, for example formulated with suitable polymeric or hydrophobic materials (e.g., as an emulsion in an acceptable oil) or ion exchange resins, or as sparingly soluble derivatives; e.g., as a sparingly soluble salt form of the ApoA-I proteins. Alternatively, transdermal delivery systems manufactured as an adhesive disc or patch which slowly releases the active ingredient for percutaneous absorption can be used. To this end, permeation enhancers can be used to facilitate transdermal penetration of the active ingredient. A particular benefit can be achieved by incorporating the ApoA-I proteins of the invention or the protein-lipid complex into a nitroglycerin patch for use in patients with ischemic heart disease and hypercholesterolemia.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Oral pharmaceutical compositions of the invention can be conjugated with NOBEX® (Protein Delivery Inc.) polymers as described in U.S. Pat. Nos. 5,359,030; 5,438,040; 5,681,811; 6,191,105; 6,309,633 and 6,380,405. Liquid preparations for oral administration can take the form of, for example, solutions, syrups or suspensions, or they can be presented as a dry product for constitution with water or other suitable vehicle before use. Such liquid compositions can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The compositions can also contain buffer salts, flavoring, coloring and sweetening agents as appropriate. Compositions for oral administration can be suitably formulated to give controlled release of the active compound.

For buccal administration, the compositions can take the form of tablets or lozenges formulated in conventional manner. For rectal and vaginal routes of administration, the active ingredient can be formulated as solutions (for retention enemas) suppositories or ointments.

For administration by inhalation, the active ingredient can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compositions can, if desired, be presented in a pack or dispenser device which can contain one or more unit dosage forms containing the active ingredient. The pack can, for example, comprise metal or plastic foil, such as a blister pack. The pack or dispenser device can be accompanied by instructions for administration.

Stable ApoA1 protein variants or modified protein formulations of the invention that have a long shelf life can be made by lyophilizing ApoA1 protein variants or modified proteins of the invention, either to prepare bulk for reformulation, or to prepare individual aliquots or dosage units which can be reconstituted by rehydration with sterile water or an appropriate sterile buffered solution prior to administration to a subject.

The ApoA1 protein variants or modified proteins of the invention can be formulated and administered in a protein-lipid complex. This approach has several advantages since the complex should have an increased half-life in the circulation, particularly when the complex has a similar size and density to HDL, and especially the pre-β-1 or pre-β-2 HDL populations. The protein-lipid complexes can conveniently be prepared by any of a number of methods described below. Stable compositions having a long shelf life can be made by lyophilization. See, U.S. Pat. No. 6,287,590. The ApoA1 protein variant- or modified protein-lipid complex can be a pharmaceutical composition. See, U.S. Pat. No. 6,306,433. The lyophilized ApoA1 protein variant- or modified protein-lipid complexes can be used to prepare bulk for pharmaceutical reformulation, or to prepare individual aliquots or dosage units which can be reconstituted by rehydration with sterile water or an appropriate buffered solution prior to administration to a subject.

A variety of methods well known to those skilled in the art can be used to prepare the protein-lipid vesicles or complexes. To this end, a number of available techniques for preparing liposome or proteoliposome compositions can be used. For example, the ApoA1 protein variants or modified proteins of the invention can be cosonicated (using a bath or probe sonicator) with appropriate lipids to form vesicles. Alternatively the protein can be combined with preformed lipid vesicles resulting in the spontaneous formation of protein-lipid vesicles. In yet another alternative, the protein-lipid vesicles can be formed by a detergent dialysis method; e.g., a mixture of the protein, lipid and detergent is dialyzed to remove the detergent and reconstitute or form protein-lipid vesicles (See, Jonas et al., 1986, Methods in Enzymol. 128:553-582).

The lyophilized composition can be reconstituted in order to obtain a solution or suspension of the protein-lipid complex. To this end, the lyophilized powder is rehydrated with an aqueous solution to a suitable volume (often 5 milligrams protein per milliliter which is convenient for intravenous injection). In certain embodiments the lyophilized powder is rehydrated with phosphate buffered saline or a physiological saline solution. The mixture can be agitated or vortexed to facilitate rehydration, and in most cases, the reconstitution step should be conducted at a temperature equal to or greater than the phase transition temperature of the lipid component of the complexes. Within minutes, a clear solution of reconstituted lipid-protein complexes results. An aliquot of the resulting reconstituted composition can be characterized to confirm that the complexes in the preparation have the desired size distribution; e.g., the size distribution of HDL. Gel filtration chromatography can be used to this end.

The ApoA1 protein variants or modified proteins of the invention can be complexed with a variety of lipids, including saturated, unsaturated, natural and synthetic lipids and/or phospholipids. Suitable lipids include, but are not limited to, small alkyl chain phospholipids, egg phosphatidylcholine, soybean phosphatidylcholine, dipalmitoylphosphatidylcholine, dimyristoylphosphatidylcholine, distearoylphosphatidyl-choline 1-myristoyl-2-palmitoylphosphatidylcholine, 1-palmitoyl-2-myristoylphosphatidyl-choline, 1-palmitoyl-2-stearoylphosphatidylcholine, 1-stearoyl-2-palmitoylphosphatidylcholine, dioleoylphosphatidylcholine dioleophosphatidylethanolamine, dilauroylphosphatidylglycerol phosphatidylcholine, phosphatidylserine, phosphatidylethanolamine, phosphatidylinositol, sphingomyelin, sphingolipids, phosphatidylglycerol, diphosphatidylglycerol, dimyristoylphosphatidylglycerol, dipalmitoylphosphatidylglycerol, distearoylphosphatidylglycerol, dioleoylphosphatidyl-glycerol, dimyristoylphosphatidic acid, dipalmitoylphosphatidic acid, dimyristoylphosphatidylethanolamine, dipalmitoylphosphatidylethanolamine, dimyristoyl-phosphatidylserine, dipalmitoylphosphatidylserine, brain phosphatidylserine, brain sphingomyelin, dipalmitoylsphingomyelin, distearoylsphingomyelin, phosphatidic acid, galactocerebroside, gangliosides, cerebrosides, dilaurylphosphatidylcholine, (1,3)-D-mannosyl-(1,3)diglyceride, aminophenylglycoside, 3-cholesteryl-6'-(glycosylthio)hexyl ether glycolipids, and cholesterol and its derivatives.

For use in the methods and compositions of the present invention, the ApoA1 protein variants or modified proteins of the invention can be any administered by any method of administration known to those of skill in the art.

For example, the ApoA1 protein variants or modified proteins of the invention or their protein-lipid complexes can be administered by any suitable route that ensures bioavailability in the circulation. This can e.g. be achieved by parenteral routes of administration, including intravenous (IV), intramuscular (IM), intradermal, subcutaneous (SC) and intraperitoneal (IP) injections. Other routes of administration can also be used, such as absorption through the gastrointestinal tract by oral routes of administration (including but not limited to ingestion, buccal and sublingual routes) provided appropriate compositions (e.g., enteric coatings) are used to avoid or minimize degradation of the active ingredient, e.g., in the harsh environments of the oral mucosa, stomach and/or small intestine. Alternatively, administration via mucosal tissue such as vaginal and rectal modes of administration can be utilized to avoid or minimize degradation in the gastrointestinal tract. In yet another alternative, the compositions can be administered transcutaneously (e.g., transdermally), or by inhalation. The preferred route may vary with the condition, age and compliance of the patient or subject.

The ApoA1 protein variants or modified proteins of the invention or their protein-lipid complexes can be used therapeutically or prophylactically. That is, prior to or after the presence of atherosclerotic symptoms or diagnosis of atherosclerosis. The actual dose used can vary with the route of administration, pharmacokinetics and pharmacodynamics of the pharmaceutical composition, characteristics of the subject and disorder to be treated. The dose can be adjusted to achieve circulating plasma concentrations of about 5 mg/l to about 3 g/l. In certain embodiments, ApoA1 protein variants or modified proteins of the invention or their protein/lipid complexes can be administered by injection at a dose between about 0.5 mg/kg to about 100 mg/kg about once a week. In another embodiment, the dose is about 0.1 to about 1000 mg/kg/day. In another embodiment, the dose is about 0.1 to about 500 mg/kg/day. In another embodiment the dose is about 0.1 to about 100 mg/kg/day. In another embodiment, the dose is about 0.1 to about 5 mg/kg/day. In yet another embodiment, desirable serum levels can be maintained by continuous infusion or by intermittent infusion providing about 0.5-100 mg/kg/hr.

It will be apparent to one of skill in the art that the frequency of administration of the ApoA1 protein variants or modified proteins of the invention or its protein-lipid complexes can vary according to the route of administration, pharmacokinetics and pharmacodynamics of the pharmaceutical composition, characteristics of the subject and disorder to be treated.

Administration of the ApoA1 protein variants or modified proteins of the invention or their protein-lipid complexes can continue until cardiovascular risks decrease. Such cardiovascular risks can be monitored in any manner known to one of skill in the art. Cardiovascular risk monitoring can be done, for example, by measuring HDL levels, angiography, exercise tolerance and the like, as described below.

Toxicity and therapeutic efficacy of compositions comprising the ApoA1 protein variants or modified proteins of the invention can be determined using standard pharmaceutical procedures in cell culture or experimental animals for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

In addition, the pharmaceutical compositions of the invention can be administered in combination with LCAT, either purified or recombinantly made, in order to compensate for the loss of LCAT activation capacity of the modified ApoA1 protein variant or modified protein, or by using an LCAT activating molecule or chemical agent. Such combination has previously been shown to have beneficial effects on patients suffering from cholesterol-related disorders (Koukos et al., Biochem J. 406(1):167-74) to compensate the lack of LCAT activation of recombinant modified ApoA1 proteins.

In a further embodiment of the invention, we provide a method to stabilize known pharmaceutical compositions comprising ApoA1 proteins or ApoA1 protein variants in order to increase their therapeutic activity or effect, when used in pharmaceutical compositions. The method relies on the inventive concept that the ApoA1 protein comprises an internal proteolytic cleavage site, which can be blocked, thereby stabilizing the protein. The dose of a known pharmaceutical composition stabilised by the method of the invention is expected to be significantly lower then what would have to be used for the non-stabilized ApoA1 formulations.

Disorders Treatable with the Pharmaceutical Composition of the Invention

The ApoA1 protein variants or modified proteins or their protein/lipid complexes can be used to treat any disorder in animals, especially mammals including humans, for which increasing serum HDL concentration, activating LCAT, and promoting cholesterol efflux and reverse cholesterol transport (RCT) is beneficial.

Examples of such conditions include dyslipidemia, and especially hyperlipidemia, hypercholesterolemia, hypertriglyceridemia, hyperlipoproteinemia, HDL deficiency, ApoA-I deficiency and cardiovascular disease such as coronary artery disease (including, for example, treatment and prevention of angina, myocardial infarction and sudden cardiac death); atherosclerosis (including, for example, treatment and prevention of atherosclerosis); restenosis (including, for example, preventing or treating atherosclerotic plaques which develop as a consequence of medical procedures such as balloon angioplasty); and other disorders, such as inflammation, infections due to bacteria (including, for example, endotoxemia which can induce septic shock) and viruses (including, for example, influenza A and influenza B). ApoA1 is also implicated in Alzheimer's disease and age-related macular degeneration (AMD), for which a pharmaceutical composition according to the invention can be beneficial as well.

The ApoA1 protein variants or modified proteins or their protein/lipid complexes can be used to treat disorders in humans characterized by the accumulation of cholesterol within the arterial wall. The accumulation of cholesterol or plaque within arterial walls is generally a slow progressive disease. The methods of the invention can be used early in the disease process to slow the progression of cholesterol deposits or atherosclerosis, and associated co-morbid disorders. In certain embodiment of the invention, the compositions of the invention can be used to reverse atherosclerosis. In further embodiments, the compositions of the invention can be used to treat cardiovascular diseases. In certain embodiments, the composition of the invention can be used to treat or prevent disorders associated with dyslipidemia, including hyperlipidemia, HDL deficiency and the like. In certain embodiments, the compositions can promote cholesterol efflux, promote reverse cholesterol transport and participate in the delivery of cholesterol esters to the liver.

The ApoA1 protein variants or modified proteins or their protein/lipid complexes can be used alone or in combination with other drugs used to treat the foregoing conditions.

Finally, a search in the single nucleotide polymorphism (SNP) database at NCBI, revealed a non-synonymous SNP (SNP ID: rs5078) at the Arginine 184 position resulting in an amino acid substitution to Proline (ApoA1-R184P). Since proteolysis occurs rarely after a Proline due to the frequent occurrence of bends in the three-dimensional protein structure, we investigated whether this mutation prevents the ApoA1 protein from being cleaved by its natural protease. We could demonstrate that this polymorphism leads to a naturally occurring variant that is resistant to protease activity at the R184 site.

We next investigated whether this naturally occurring ApoA1-R184P-variant is indeed more stable in vitro (in blood samples) and in vivo in a mouse model. In a following experiment, we analysed whether the ApoA1-R184P-variant could indeed alter the reverse cholesterol transport in a mouse model, deficient for ApoA1.

Further, the invention provides diagnostic applications such as a method for analyzing the cholesterol balance in a patient comprising the detection of a mutation in the isolated APO A1 protein of a patient leading to a stabilisation or increased half-life of the protein, wherein the mutation is an Arg to Pro modification at amino acid position 184 of the prepro-ApoA1 amino acid sequence as defined in SEQ ID NO: 2 (FIG. 2b), wherein detection of the mutation points to a favourable cholesterol balance in the patient due to stabilisation of the ApoA1 protein. In one embodiment, the mutation is detected on the protein level. In a further embodiment, the mutation is detected on the nucleotide level. The carriers of this allele can be easily identified by genetic screening using e.g. PCR analysis of their genetic material obtained from a blood sample.

By analyzing serum samples from healthy human subjects with the N-terminal identification method, the inventors discovered that naturally occurring proteolysis leads to the formation of an unexpectedly high amount of peptides derived from naturally synthesised proteins.

The method of the invention can in general be used for the analysis of the N-terminal proteins in a complex protein sample after the naturally occurring proteolysis, followed by analysis and identification of the peptides in the mixture. Besides identifying the true N-terminus of the proteins in the mixture e.g. after maturation and cleavage of pre and pro domains, the N-terminal peptide-identification technology of the invention also allows the characterisation of novel N-termini that are generated by naturally occurring proteolysis.

In this respect, the invention provides a method for the identification of proteolytic cleavage sites in a protein in a complex mixture in encompassed comprising;
a) extracting the peptides of the protein under investigation using a specific antibody or a mixture of specific antibodies,
b) protecting the natural N-termini of the proteins obtained in step a) by e.g. acetylation or ICPL
c) cleavage of the extracted proteins in the mixture into peptides with e.g. trypsin,
d) separating the protected peptides from the non-protected proteins
e) analysing the protected N-terminal peptides by mass-spectrometry,
f) identifying the internal proteolytic cleavage site(s) in said protein.

In some embodiments, step d) can be done using an aminopeptidase step, degrading all non-protected peptides, only leaving the protected peptides in the sample. Alternatively, a bead-like system can be used to capture and separate the protected peptides form the non-protected peptides.

Preferably, the sample is a bodily fluid selected from the group consisting of blood (e.g., plasma or serum), cerebrospinal fluid, saliva, urine, nipple aspirate, ductal ravage, sweat or perspiration, tumor exudates, joint fluid (e.g. synovial fluid), inflammation fluid, tears, semen and vaginal secretions.

The invention further provides for a method for stabilising or increasing the half-life of a protein comprising;
a) identifying the proteolytic cleavage site(s) in the protein using the method above,
b) modifying the identified proteolytic cleavage site(s) in the protein such that the protein can no longer be cleaved at said site(s).

This modification can e.g. be done by introduction of a point mutation in the coding sequence of the protein at a position surrounding the identified proteolytic cleavage site, thereby altering the amino acid sequence of the protein and subsequently blocking proteolytic cleavage.

Alternatively, the modification is done by chemical modification of a side chain of the amino acid residues surrounding the identified proteolytic cleavage site, blocking proteolytic cleavage.

The protein can be a known or yet unknown therapeutic protein, which is either purified from a sample or is recombinantly made, with the potential to significantly reduce dosing of these proteins. Small molecules targeting the responsible proteases for these proteins can be valid here as well. The generation of such protease-resistant proteins results in proteins that have prolonged activity (longer half-lives) when used for therapeutic applications. It is clear that N- or C-teromics technology is also able to detect protease sensitive sites during the production process. Elimination of such sites can result in benefits for production. This is for instance true for proteins that are produced in the milk of e.g. transgenic animals.

In particular, the analysis in step e) of the method above is done by using a reversed phase-high performance liquid chromatography system connected to an electrospray ionization mass spectrometry, ion trap mass spectrometry, hybrid ion trap mass spectrometry, time-of-flight mass spectrometry, ion trap-fourier transform mass spectrometer.

EXAMPLES

The invention is illustrated by the following non-limiting examples

Example 1

N-terminal Analysis to Detect ApoA1 Processing

The COFRADIC N-terminal proteomics platform allows us to specifically analyse the N-terminus of a protein (or of a number of proteins), but in addition application of such a strategy also reveals proteolytic processing as these novel N-termini are also readily detected. Application of this platform on a serum sample revealed the occurrence of a novel cleavage event in human Apolipoprotein A1 (Swissprot accession: APOA1_HUMAN) after position R184.

Protocol:

Delipidation and Affinity Removal of 6 Abundant Proteins

Serum from a healthy volunteer was prepared according to standard procedures. One volume of TBS (100 mM Tris-HCl pH7.4, 150 mM NaCl) and one volume of trichlorotrifluoroethane (Riedel-de-Haën, #34874) are added to a 120 μl serum sample. After vortexing and centrifugation, the delipidated sample is transferred to a new vial and diluted 2.5× with MARS buffer A complemented with protease inhibitors. The sample is depleted with MARS level I column according to the manufacturer's description (Multiple Affinity Removal System LevelI, Agilent).

Reduction/Alkylation and Acetylation

Guanidiniumhydrochloride (GdnHCl) is added to the depleted sample to obtain a final concentration of 3M. TCEP (TCEP.HCl, Pierce #20490) is added at 25 molar excess (when average size of proteins is expected to be 30 kDa) to reduce S—S bridges and the sample was incubated for 10' at 30° C. Iodoacetamide (Fluka #57670) for alkylation of sulfhydryl groups was added at a 50 molar excess and left for 60' at 30° C. Desalting was performed using PD10 columns resulting in a buffer swap to 50 mM sodiumphosphate pH 8.0, 1.4 M GdnHCl. For blocking of N-termini sulfo-NHS-acetate (Pierce #26777) is added to the sample at a 75 molar excess for 90' at 30° C. $NH_2OH$ is used to remove unwanted side reactions with serine, threonine and tyrosine (3 molar excess compared to sulfo-NHS-acetate). The sample was desalted again by PD10 to 10 mM $NH_4HCO_3$ buffer. Trypsin digestion was performed after heating the sample to 99° C. for 5'. A 50:1 (w:w) substrate:trypsin ratio was employed for ON digestion at 37° C.

COFRADIC Primary and Secondary Runs, Nano-LC Fractionations

An estimated 500 μg of peptide material in 3M GdnHCl was acidified with TFA and was fractionated in the primary run to 12 fractions using C18 Reverse Phase columns (Zorbax 300SB-C18, Agilent) on a HPLC1100 series instrument. All fractions were subsequently dried by vacuum centrifugation at 50° C., re-dissolved in 50 μl 100 mM Borate solution pH 9.5 and treated 3 times with tri-nitro-benzene-sulfonic acid (10 μl of 15 mM TNBS stock, Fluka #92822) to modify internal non-blocked peptides. The 12 collected fractions were run again under identical conditions to separate the TNP-peptides from the unblocked peptides. 32 fractions were collected for each primary run, resulting in a total of 384 fractions for this secondary run.

These 384 peptide fractions were pooled in 48 fractions after adding solvent A (0.1% FA) according to a scheme for maximal separation. These fractions were then used for NanoLC separation using an Ultimate 3000 system (Dionex) equipped with a C18 PepMap 100 column. Direct spotting on MALDI targets was realized with a Probot system (Dionex). CHCA matrix (α-cyano-4-hydroxy-cinnamic acid, Laser Bio Lab # M101) and internal standard peptides (Proteomix, Laser Bio Lab # C104) were added to the flow for optimal matrix crystal formation. Maldi targets were provided by Applied Biosystems (Opti-TOF LC/MALDI insert, # 1018469). 198 spots for each of the 48 fractions resulted in a total of 12 MALDI target plates.

MS/MS Analysis and Search Settings

MS and MS/MS measurements were performed on a 4800 MALDI-TOF/TOF machine (Applied Biosystems) in the positive reflectron mode using internal calibration. The scan range for the MS spectra stretched from 500-4000 Da. A list of the top 20 signals, per MS spectrum was generated and MS/MS experiments were performed under "metastable precursor on" conditions, without the use of CID (collision induced dissociation) and at 1 keV. The precursor mass window was set at a resolution of 250 FWHM (full width half maximum). Unfiltered MASCOT generic files (mgf) were subsequently searched against both standard and ragged human Sprot databases using MASCOT as search engine. The latter database was used to detect N-terminally ragged peptides which are abundantly present in serum. As search settings for MASCOT, we used as variable modifications pyro forms of glutamine, asparagine and cysteine, methionine oxidation and acetylation at the N-terminus, and as fixed modifications alkylated cysteine and acetylated lysine. Only peptides ranking #1 with scores above the 95% probability threshold were withheld. Spectra that had multiple peptide hits above the probability threshold were regarded as unidentified. Random hits were determined by searching the data against randomized databases. Proteins were reported if they had at least 1 peptide that unequivocally defines it.

Result:

The numbers of identified acetylated peptides within ApoA1 were mapped on the ApoA1 sequence as it was entered in the SwissProt database (ApoA1_HUMAN). The number of identifications in the described platform can be considered a semi-quantitative readout for abundancy of the different (proteolytic) variants within a protein. However this number also reflects retention (spreading of the peptide on the columns) and ionisation/fragmentation behaviour of the identified peptides, and is thus not an ideal measure.

We identify the N-terminus of the processed ApoA1 protein starting at position 25 (after removal of the signal and the propeptide). In addition, we have also identified an acetylated peptide starting at position 185 for a high number of times, suggesting extensive cleavage of the protein at this site (FIG. 1).

Example 2a

Western Analysis for ApoA1 Variants in Blood of a Healthy Person

Using antibodies directed against the N- and C-terminus of ApoA1 in Western analysis, we are able to identify the naturally occurring variants of this protein that can be found in the blood of a normal healthy person. This confirms the data obtained with the N-terminal discovery platform described higher.

Protocol:

Serum samples from healthy donors (appr. 2 μl or 100 mg) are diluted to 16 ul with Phosphate Buffered Saline (0.2M Phosphate pH7.4, 150 mM NaCl). 4 μl 5× Loading buffer is added (0.313 M Tris-HCl pH 6.8, 10% SDS, 0.05% bromophenol blue, 50% glycerol). The sample is heated to 99° C., and after cooling loaded on 15% SDS-PAGE gels (Biorad, Tris-HCl ready gel). After separation, the protein material is transferred to Immobilon-P$^{SQ}$ (Millipore) membranes by electroblotting. Membranes are subsequently blocked by milk powder (2%) dissolved in TBS-T (100 mM Tris-HCl pH7.4; 150 mM NaCl; 1/1000 Tween20) for 30 min. to 1 hr. The EP1368 antibody is diluted 1/20000 in TBS-T milk, and used for incubation of the protein blot for 1 hr at RT. The ab33470 is diluted to 1.5 µg/ml in TBS-T milk and left for 1 hr at RT on the blot. After washing with TBS-T (4×5 min.), secondary antibody (Donkey polyclonal to rabbit IgG, HRP coupled, ab16284) is diluted 1/2500 in TBS-T milk, and left on the blot for 30 min. to 1 hr. After washing with TBS-T (4×5 min.), the blot is developed using Amersham Hyperfilm™ ECL Bioscreen, Hypercassette™ (both from Amersham Biosciences) and standard photo development equipment (Kodak AL4).
Results:
At least 2 species are detected: the full length form of about 30 kDa and a processed C-terminal fragment of about 10 kDa. This observation implies that the processing of ApoAI does not occur post-sampling, but rather in vivo. In plasma, the N-terminus starting at position 185 can also be detected (see higher), suggesting that processing does not occur during serum preparation.

Example 2b

Immunological Detection of the C-terminal Fragment in ApoA-1

As an alternative detection system to show processing of ApoA-1, we used a classic immunological approach. The AI-4.1 mouse monoclonal antibody detects specifically the ApoA-1 sequence and was obtained by immunization of BALB/c mice with the C-terminal fragment of ApoA-1 obtained after cyanogen bromide cleavage of the protein (Allan C. et al., 1993, Biochem J, 290, 449-455). This fragment corresponds to amino acid sequence 173-267 of the full length ApoA-1 protein. Processing in ApoA-1 occurs at position R184. The size predicted for the C-terminal fragment based on this cleavage is 9.3 kDa.
Serum obtained from healthy males was pooled and depleted using the Multiple Affinity Removal System (MARS) level I (Agilent) removing the 6 most abundant proteins (albumin, alfa-1-antitrypsin, haptoglobin, IgG, IgA, transferrin). 3× Loading buffer (125 mM Tris-HCl/4% SDS/ 50% glycerol/0.02% Bromophenol Blue/10% beta mercaptoethanol) was added to the depleted serum (at 250 µg/ml) after a 2 fold concentration of the sample. Approximately 10 µg was loaded on the SDS-PAGE gel. A 4-20% gradient gel (Precise gel, Pierce) was used to separate the protein sample. The Kaleidoscope prestained marker (Biorad) was loaded for molecular weight reference. After separation, the protein material was transferred to Immobilon-P$^{SQ}$ membranes (Millipore) by electroblotting. The membrane was blocked with blocking buffer (5% BSA in TBS) followed by probing with the primary antibody AI-4.1 directed against the C-terminus of ApoA-1. To this end, a 1/15 dilution of crude mouse hybridoma supernatant in incubation buffer (0.5% BSA in TBS+ 0.1% Tween20) was used. After washing, secondary antibody was added at a 1/6000 dilution in incubation buffer. HRP activity was revealed by using the West pico chemiluminescence substrate (Pierce) and Hyperfilm™ ECL films (Amersham) using a Hypercassette™ (Amersham) in combination with an automated developer (Fujifilm S/N244-FPR-001).

The western blot confirms a processing event of the expected size in the depleted serum of male donors. As the antibody was specifically raised against the C-terminal part starting from amino acid 173, and the size of the observed fragment is close to the size of this C-terminal part, it can be expected that the observed ApoA-1 starts very close to position 173, which fits with the observation of a processing event after R184 in the COFRADIC analysis of example 1.

Example 3

Analysis of the Stability of the ApoA1-R184P-mutant and Wild-type ApoA1

Wild-type (WT) ApoA1 and ApoA1 variants with mutated cleavage sites are produced recombinantly in bacteria to monitor stability of the protein in blood. Different mutants are generated by mutagenesis of the expression construct. We opted for a R184-P mutant, as this mutation naturally occurs in some carriers, and for the R184-H mutant which is expected to have less effect on the secondary structure of the protein. Other mutations surrounding the R184 site as exemplified above were introduced as well.
Protocol:
The cDNA of human ApoA1 in the pENTR™221 vector (clone ID: IOH7318, Gateway® system, Invitrogen) can be used as template DNA for a site directed mutagenesis reaction. Mutagenic primers comprising the sequence for the mutated amino acid are used in the PCR reaction of the Quickchange™ mutagenesis kit. An additional restriction site alteration is introduced by the mutagenic primers to facilitate detection of mutated sequences. After verification of mutated sequences by sequencing, the cDNA sequence is transferred to the pET11d expression vector (Novagen) by recombination-assisted cloning, direct transfer with compatible restriction enzymes, or by PCR-based cloning. The signal sequence is omitted in the final expression construct and is replaced by a N-terminal HIS-tag to empower purification by nickel affinity chromatography. The HIS-tag is followed by a TEV protease cleavage site. Inducible expression is obtained with the BL21 bacterial system. A number of mutated constructs were created that have mutations at and around the R184 site. After expression, the proteins are purified by nickel affinity chromatography. Further purification is obtained by gelfiltration with optimal resolution in the Mr 30000 range.
The protein sample can then be used for spiking in blood or serum. Different quantities of the recombinant proteins (8-40-200-1000 µg/ml) are diluted in serum. Samples are collected at different timepoints (t0, 30', 1 hr, 2 hr, 4 hr, 8 hr, 16 hr) and used for Western analysis. For these experiments the HIS-tag is not removed by TEV protease activity. Stability is monitored by Western blot directed against the HIS-tag. Mouse monoclonal anti-HIS-tag antibody is provided by R&D systems (MAB050) and is used at 1 µg/ml in TBS-T/ milk solution. Secondary HRP-coupled donkey anti-mouse antibody is from Abcam (ab7061) and is used for revelation at 0.5 µg/ml in TBS-T/Milk.
Results:
Western analysis can reveal prolonged half-lives for ApoA1 proteins carrying mutations in the R184 site. Sensitivity to proteolytic activity is expected to be reduced in these mutants.

Example 4

Stability of ApoA1 Variants in Mice

For further evaluation of ApoA1 stability, in vivo experimentation in mice is employed. Recombinant proteins are administered to mice deficient in ApoAI, and the stability in blood is monitored by Western analysis. The difference in HDL levels after administering the different ApoA1 variants is evaluated by FPLC separation of mouse plasma followed by quantification of cholesterol, phospholipids and triglycerides in the different fractions, where higher fractions correspond to HDL particles.

Protocol:

ApoI deficient mice (B6.129P2-Apoa1$^{tm1Unc}$/J, Jackson Labs) are injected intravenously with the recombinant protein preparations described higher. Injections of recombinant ApoA1 proteins to obtain a final concentration of 40, 200 and 1000 mg/ml in blood will be used to better visualize increased stability.

Stability of the proteins in serum is monitored by using anti-HIS antibody and Western blot. In addition, the HIS tag is removed from the recombinant proteins by TEV protease treatment. After intravenous injection of the processed and purified proteins, stability is monitored by Western blotting using the procedure and the antibodies described in part 1.

Fast protein liquid chromatography (FPLC) is used to fractionate mouse plasma. 20 µl of mouse plasma is fractionated on a Sepharose 6 PC column (GE Healthcare) and eluted with PBS. 25 fractions of 50 µl volume each are collected. Levels of total cholesterol and phospholipids in the fractions are determined using the Cholesterol CII and the Phospholipids B kit respectively (both from Wako Chemicals USA, Inc.).

Triglyceride content in the fractions is monitored by INFINITY triglycerides (Thermo DMA). Total ApoA1 levels are determined using Autokit ApoA1 (Wako Diagnostics USA, Inc), and are verified by Western blot using the protocol and the antibodies described higher. Higher FPLC fractions correspond to the HDL particles (fractions 14-20) while VLDL and LDL can be found in the lower FPLC fractions (respectively in fractions 1-9 and fractions 10-13).

Results:

The concentration of total cholesterol, phospholipids and ApoA1 is expected to be significantly larger in the HDL fractions for the mutant proteins when compared to the wild type protein, suggesting an accumulation of functional mutant ApoA1 in these particles. An increased formation of these HDL particles suggests increased reverse cholesterol transport and implies an improved efficacy of recombinant ApoA1 R184 mutants when used for treatment of cardiovascular disease.

Example 5

Linkage of the ApoA1 R184→P Genetic Variation to Increased HDL Levels in Carriers A previous study shows the occurrence of a natural genetic variation (SNP) resulting in a R184→P alteration (NCBI SNP ID: rs5078). The study was initiated to evaluate genetic variation in a list of candidate genes linked to blood pressure homeostasis.

Protocol:

A large study population of people with high levels of HDL (in upper 2.5 percentile of population) and people with normal levels of HDL is used for sequencing of the affected region. Primers were designed to amplify the genomic region containing the genetic variation. The occurrence of the R184→P variation is counted in the complete study population and is tested for statistically significant linkage to high HDL levels.

Results:

Linkage of the R184→P genetic variation to increased HDL levels is to be expected, supporting increased stability of this ApoA1 variant, resulting in increased HDL levels.

The invention claimed is:

1. A method for producing a stabilised, protease resistant ApoA1 protein variant comprising
   a) modifying the ApoA1 protein either by amino acid substitution or by chemical modification of the amino acid side chains at the R184 position in the amino acid sequence of ApoA1 as defined in SEQ ID NO: 2,
   b) analysing the proteolytic cleavage of the modified ApoA1 protein to confirm that a stabilised, protease resistant ApoA1 protein variant has been produced.

2. The method of claim 1, additionally comprising the following step:
   c) analysing the lecithin:cholesterol acyltransferase (LCAT) activation efficiency of the Apo1A variant.

3. A recombinant stabilised ApoA1 protein variant modified at the R184 position in the amino acid sequence of ApoA1 as defined in SEQ ID NO: 2, which is protease-resistant and wherein said modification is selected from the group consisting of R184P, R184K, and R184H of SEQ ID NO:2.

4. A reconstituted HDL (rHDL) particle comprising the recombinant protease-resistant ApoA1 variant according to claim 3.

5. A pharmaceutical composition comprising the reconstituted HDL (rHDL) particle of claim 4.

6. A method for treating a disease or disorder linked to ApoA1 comprising administering to a patient a pharmaceutically active amount of the reconstituted HDL particle according to claim 4 effective to increase HDL concentration, activating lecithin:cholesterol acyltransferase (LCAT), and/or promoting cholesterol efflux and reverse cholesterol transport (RCT), wherein said disease is selected from the group consisting of: dyslipidemia, hyperlipidemia, hypercholesterolemia, hypertriglyceridemia, hyperlipoproteinemia, HDL deficiency, ApoA-I deficiency, cardiovascular disease, coronary artery disease, angina, myocardial infarction, sudden cardiac death, atherosclerosis, restenosis, atherosclerotic plaques, and atherosclerotic plaques resulting from a medical procedure of balloon angioplasty.

7. A method for treating a disease or disorder linked to ApoA1 comprising administering to a patient a pharmaceutically active amount of the recombinant protease-resistant ApoA1 variant according to claim 3 effective to increase HDL concentration, activating lecithin:cholesterol acyltransferase (LCAT), and/or promoting cholesterol efflux and reverse cholesterol transport (RCT), wherein said disease is selected from the group consisting of : dyslipidemia, hyperlipidemia, hypercholesterolemia, hypertriglyceridemia, hyperlipoproteinemia, HDL deficiency, ApoA-I deficiency, cardiovascular disease, coronary artery disease, angina, myocardial infarction, sudden cardiac death, atherosclerosis, restenosis, atherosclerotic plaques, and atherosclerotic plaques resulting from a medical procedure of balloon angioplasty.

8. A method for stabilising a known pharmaceutical composition in which the ApoA1-protein or a variant or modified protein thereof is the active ingredient, the method comprising modifying the ApoA1 protein at the R184 position in the amino acid sequence of ApoA1 as defined in SEQ ID NO: 2 either by amino acid substitution or by chemical modification of the amino acid side chains in such a way that proteolytic cleavage of the active ingredient is blocked.

9. The method of claim 8, wherein the active ingredient is the recombinant ApoA1 protein variant, a rHDL particle comprising the recombinant ApoA1 protein variant or a multimer of the ApoA1 protein variant.

* * * * *

SEQUENCE LISTING

<160> NUMBER OF SEQ ID NOS: 2

<210> SEQ ID NO 1
<211> LENGTH: 897
<212> TYPE: DNA
<213> ORGANISM: Homo sapiens

<400> SEQUENCE: 1

```
agagactgcg agaaggaggt cccccacggc ccttcaggat gaaagctgcg gtgctgacct      60
tggccgtgct cttcctgacg gggagccagg ctcggcattt ctggcagcaa gatgaacccc     120
cccagagccc ctgggatcga gtgaaggacc tggccactgt gtacgtggat gtgctcaaag     180
acagcggcag agactatgtg tcccagtttg aaggctccgc cttgggaaaa cagctaaacc     240
taaagctcct tgacaactgg gacagcgtga cctccacctt cagcaagctg cgcgaacagc     300
tcggccctgt gacccaggag ttctgggata acctggaaaa ggagacagag ggcctgaggc     360
aggagatgag caaggatctg gaggaggtga aggccaaggt gcagccctac ctggacgact     420
tccagaagaa gtggcaggag gagatggagc tctaccgcca gaaggtggag ccgctgcgcg     480
cagagctcca agagggcgcg cgccagaagc tgcacgagct gcaagagaag ctgagcccac     540
tgggcgagga gatgcgcgac cgcgcgcgcg cccatgtgga cgcgctgcgc acgcatctgg     600 cccctacag cgacgagctg cgccagcgct tggccgcgcg ccttgaggct ctcaaggaga     660
acggcggcgc cagactggcc gagtaccacg ccaaggccac cgagcatctg agcacgctca     720
```

```
gcgagaaggc caagcccgcg ctcgaggacc tccgccaagg cctgctgccc gtgctggaga    780
gcttcaaggt cagcttcctg agcgctctcg aggagtacac taagaagctc aacacccagt    840
gaggcgcccg ccgccgcccc ccttcccggt gctcagaata aacgtttcca aagtggg       897
```

```
<210> SEQ ID NO 2
<211> LENGTH: 267
<212> TYPE: PRT
<213> ORGANISM: Homo sapiens

<400> SEQUENCE: 2

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265
```